United States Patent [19]

Attaoui et al.

[11] Patent Number: 5,537,334

[45] Date of Patent: Jul. 16, 1996

[54] PROCESS FOR PROCESSING SIGNALS COLLECTED BY AN EDDY CURRENT ABSOLUTE POINT TRANSDUCER

[75] Inventors: Pascale Attaoui, Chatenay-Malabry; Bruno Benoist, L'Hay-les-Roses; Rémy Besnard, Magny les Hameaur; Bernard David, Gif-sur-Yvette, all of France

[73] Assignee: Commissariat a l'Energie Atomique, Paris, France

[21] Appl. No.: 130,186

[22] Filed: Oct. 1, 1993

[30] Foreign Application Priority Data

Oct. 7, 1992 [FR] France .................................. 92 11893

[51] Int. Cl.⁶ .................................................. G06F 17/00
[52] U.S. Cl. ........................ 364/507; 364/506; 364/505
[58] Field of Search ................................ 364/505–508; 324/237, 238, 240, 222, 262, 306, 234, 309, 292, 219, 220, 228; 382/29, 41–43; 73/575, 594, 598, 600, 602, 626, 632, 634; 348/92, 84, 83, 82, 125, 128, 180, 139, 90, 136, 347

[56] References Cited

U.S. PATENT DOCUMENTS

| | | | |
|---|---|---|---|
| 4,203,069 | 5/1980 | Davis | 324/228 |
| 4,303,885 | 12/1981 | Davis et al. | 324/237 |
| 4,476,434 | 10/1984 | Collins et al. | 324/262 |
| 5,006,800 | 4/1991 | Hedengren et al. | 324/237 |
| 5,117,182 | 5/1992 | Cecco et al. | 324/242 |
| 5,140,265 | 8/1992 | Sakiyama et al. | 324/237 |
| 5,182,513 | 1/1993 | Young et al. | 324/242 |
| 5,210,492 | 5/1993 | Hosohara et al. | 324/242 |
| 5,256,966 | 10/1993 | Edwards | 324/238 |
| 5,311,128 | 5/1994 | Lareau et al. | 324/237 |
| 5,345,514 | 9/1994 | Mahdavieh et al. | 324/240 |
| 5,424,640 | 6/1995 | Levy | 324/240 |

FOREIGN PATENT DOCUMENTS

| | | |
|---|---|---|
| 0411874 | 2/1991 | European Pat. Off. |
| 2192993 | 1/1988 | United Kingdom . |

OTHER PUBLICATIONS

IEEE Transactions on Magnetics, vol. 27, No. 6, Nov. 1991, Riadh Zorgati, et al., "Eddy Current Testing of Anomalies in Conductive Materials, Part 1: Qualitative Imaging via Diffraction Tomography Techniques", pp. 4416–4437.

ICASSP 86 Proceedings, Apr. 1986, P. Simard, et al., "Automatic Classification and Recognition of Defects in an Eddy Current Non Destructive Testing", pp. 1441–1444.

IEEE Transactions on Magnetics, vol. MAG–20, No. 5, Sep. 1984, R. O. McCary, et al., "Eddy Current Imaging", pp. 1986–1988.

*Primary Examiner*—Emanuel T. Voeltz
*Assistant Examiner*—Hal P. Wachsman
*Attorney, Agent, or Firm*—Oblon, Spivak, McClelland, Maier & Neustadt

[57] ABSTRACT

A system for the processing of signals collected by an eddy current absolute point transducer moving along an inner surface of a conductive material tube and supplying a representative signal concerning the state of the inner surface. The system incorporates a stage for scanning the surface in accordance with a given order or sequence of elementary measurement zones and recording the sampled values of the signal supplied by the transducer for each of the elementary zones, which makes it possible to obtain a three-dimensional image representative of the surface. The system also constructs a background noise surface on the complete image, subtracts the background noise surface from the image and detects a defect or fault on the surface. Such an invention may find particular application to the inspection of steam generator tubes.

7 Claims, 5 Drawing Sheets

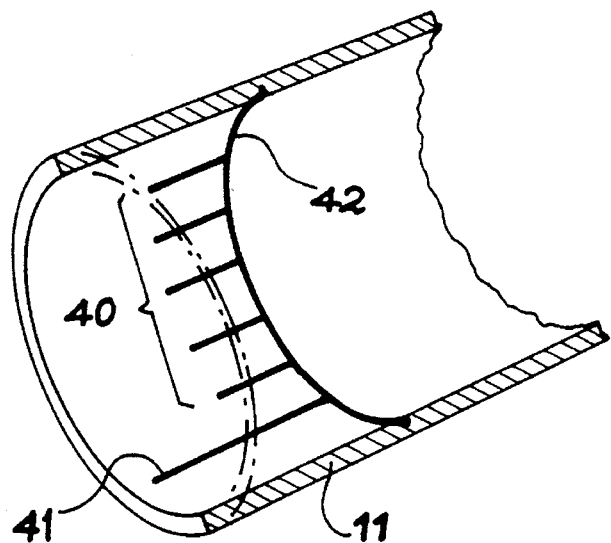
FIG. 7A
FIG. 7B
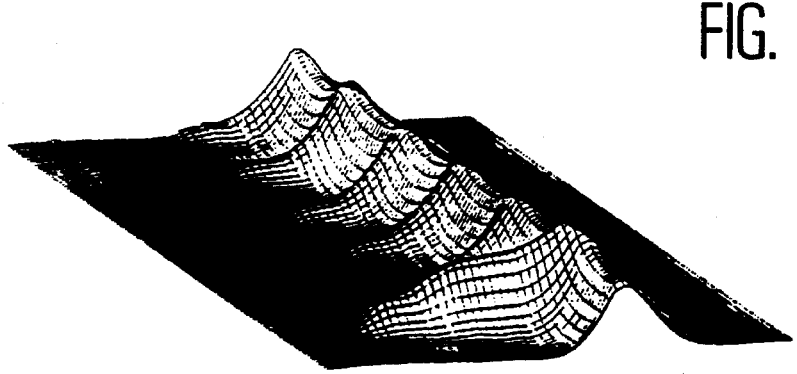
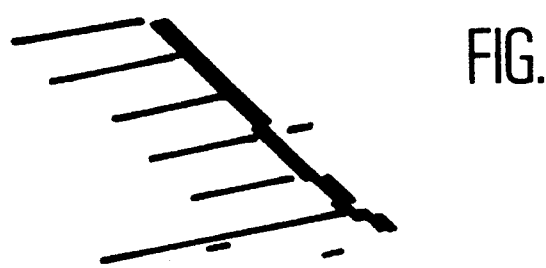
FIG. 7C

PROCESS FOR PROCESSING SIGNALS COLLECTED BY AN EDDY CURRENT ABSOLUTE POINT TRANSDUCER

TECHNICAL FIELD

The present invention relates to a process for processing signals collected by an eddy current absolute point or punctiform transducer moving along the inner wall of a tube, or cylindrical apparatus made from conductive material. The invention is used in the inspection of steam generator tubes.

PRIOR ART

It is known to inspect the surface of electricity conducting material parts by using eddy current transducers. The signal supplied by such transducers gives information on the surface state and the possible presence of faults or defects on moving the transducer in front of the surface. For example, an inspection of this type is periodically carried out in the tubes of heat exchangers or steam generators equipping nuclear power stations.

No matter what the envisaged application, such an inspection procedure consists of carrying out a maximum complete scan of the surface to be inspected and observing by means of a direct reading system the variations of the signal supplied by the transducer in order to deduce therefrom the state of the inspected surface.

On using as an example pressurized water nuclear power stations, bars containing uranium are placed in a water-filled vessel. The water heats in contact with the bars and then transmits its heat to a heat exchanger, where cooling takes place and is then returned to the vessel by a pump. Thus, the water circulates in a closed circuit manner. The heat exchanger serves as a steam generator. The water of a second circuit is vaporized on contact with the hot tubes of the primary circuit. The steam drives a turbine coupled to an alternator and then, following condensation, the water obtained is returned to the steam generator. Finally, in order to condense the steam, cold water is circulated in a third circuit. Thus, such a power station has three independent circuits, namely the primary circuit transmitting the heat of the reactor, the secondary "water-steam" circuit and the cooling circuit.

Each steam generator with a height of about 20 meters has in its lower part a horizontal plate perforated by a large number of holes. Below the plate a vertical wall separates the primary water supply and discharge compartments. Above the plate are positioned several thousand inverted U-tubes, whose ends are welded in the holes of the horizontal plate.

It is in contact with these tubes, traversed by the hot water of the primary circuit, that the secondary circuit water vaporizes and on transmitting its heat, the water of the primary circuit is cooled from 320° C. at the entrance to 280° C. at the exit.

The monitoring of such a steam generator consists of detecting any fault which might realize the communication between the primary water circuit and the secondary water circuit at the tubes. Therefore checks or inspections are periodically carried out using the eddy current method.

As a nuclear installation ages, the inspection of such tubes causes new problems. Thus, new defects appear, particularly at the tube plates, bracing plates or bow entrances. The measurements carried out on the tubes are obtained from an eddy current probe. Such a probe comprises an electric coil inserted in a measuring bridge. The impedance variations of the coil during its displacement in the tube bring about an unbalance of the bridge, which constitutes the useful information. The performance characteristics of conventional axial probes with regards to the detection of new defects are inadequate and have led to the development of a new absolute point transducer probe. This data supply means makes it possible to detect very small defects and in accordance with different orientations, particulary circumferential defects in expansion transitions. The useful information is therefore contained in the signal acquired during the squaring of the inner surface of the tube by the probe. The representation takes place in the form of maps of each of the components of the signal in the complex plan.

French patent application 81 1731 2 of Sep. 16 1981 describes a process and an apparatus for inspecting the surface of an electricity conducting material part by means of an eddy current transducer supplying a signal representative of the state of the surface. This process consists of carrying out with the transducer a scan in a given sequence of elementary measurement zones defined on the surface of the part, recording sampled values of the signal signalled by the transducer for each of these elementary measurement zones and restoring the signals obtained from one or more sampled values corresponding to zones close to the surface in a random desired order.

The process described in the application makes it possible to obtain a map of points giving a three-dimensional vision of the inspected part, developed in accordance with a generatrix, which makes it possible to carry out a visual diagnosis. However, this is very difficult to formulate and no defect analysis tool exists.

The images obtained by the process are usually disturbed by a background noise due to gap variations of the probe particularly in the case of a tube being out of true, a probe offcentring or a rolling defect. There are two alternatives for obviating the background noise, namely improving the probes used, or processing the signal on leaving the conventional probes.

The invention proposes using a conventional probe and processing its output signal. It aims at "flattening" the image by eliminating the background noise without deteriorating the useful information contained in the image, so as to permit the analysis of a possible defect.

Moreover, in the prior art apparatuses, one of the two channels was exploited, corresponding to the projection of the signal on the Y axis of the impedance plane. Thus, the measurement and calibration process aligns the signals of the geometrical background noise with the horizontal (X axis of the impedance plane) making the projections on said axis excessively disturbed for the supply of a useable map.

The information loss relative to the map makes it impossible to calculate the phase of the signal and therefore the depth of a possible fault or defect.

The invention aims at supplying an information relative to all the characteristics of such a fault.

SUMMARY OF THE INVENTION

The invention therefore relates to a process for the processing of signals collected by an eddy current absolute point transducer travelling along the inner surface of a conductive material tube and supplying a signal representing the state of the inner surface, the process having a stage of scanning said surface in a given order of elementary measuring zones and recording sampled values of the signal supplied by the transducer for each of these zones, which makes it possible to obtain a three-dimensional image representative of the surface, characterized in that it also comprises a stage of resolving the image related to a Fourier series resolution, in order to determine the most representative components from the energy standpoint, a stage of constructing a background noise surface on the complete image, a stage of subtracting the background surface from the image and a stage of interpreting any fault.

Advantageously, the eddy current absolute point transducer comprises a point coil performing an absolute measurement according to a helical movement within the tube.

Advantageously, for obtaining an information concerning all the characteristics of a possible fault, the process according to the invention also comprises a stage of resolving the image related to a Fourier series resolution, in order to determine the most representative components from the energy standpoint, with a prior stage of defining elementary surfaces.

Advantageously, each of the elementary surfaces is the product of two base functions respectively defined in the longitudinal direction and in the circumferential direction of the tube, the functions being e.g. sinusoidal functions.

Advantageously, there is an iteration of the stages of resolving the image, constructing the background noise surface and subtracting said surface until the background noise is eliminated.

Advantageously, in order to obtain an information concerning all the characteristics of a possible fault, the process according to the invention comprises a prior stage of detecting a window or slot containing a fault or defect. Moreover, in the elementary surface definition stage, definition takes place of a first surface based $g_{i,j}$ defined by portions on the same zone as the image deprived of the fault window and a second surface base $H_{i,j}$ defined on the complete zone of the image.

Advantageously, following detection of the fault window, there is a truing preprocessing, in order to render equivalent the first and last column of the image, in which subtraction takes place of a line joining the extreme points of the image.

The process of the invention also aims at obtaining freedom from the expansion signal in order to supply a "flattened" map, where only the faults to be characterized remain.

Thus, the process according to the invention involves an expansion signal suppression preprocessing stage during which extraction takes place of several longitudinal rows of the image outside the fault window, the mean value is calculated, the corresponding surface generated and the surface is subtracted from the image.

The difficulties encountered in performing the process according to the invention are essentially due to the choice of the function base and in particular the development of preprocessing operations making it possible to obtain a reliable method in all cases. The processed examples and development took place on real files (acquisition in situ and on mock-up).

The major interest of such a process is that it considerably improves the signal to noise ratio of the image prior to analyzing the faults.

BRIEF DESCRIPTION OF THE DRAWINGS

FIGS. 7 A to 7 C Illustrate the fault skeletization phase.

DETAILED DESCRIPTION OF AN EMBODIMENT

In the remainder of the description, consideration will be given to a non-limitative embodiment of an application of the process of the invention to the inspection of steam generator tubes. However, obviously other applications are possible within the scope of the inspection of conductive material, cylindrical equipment.

Figure 1:
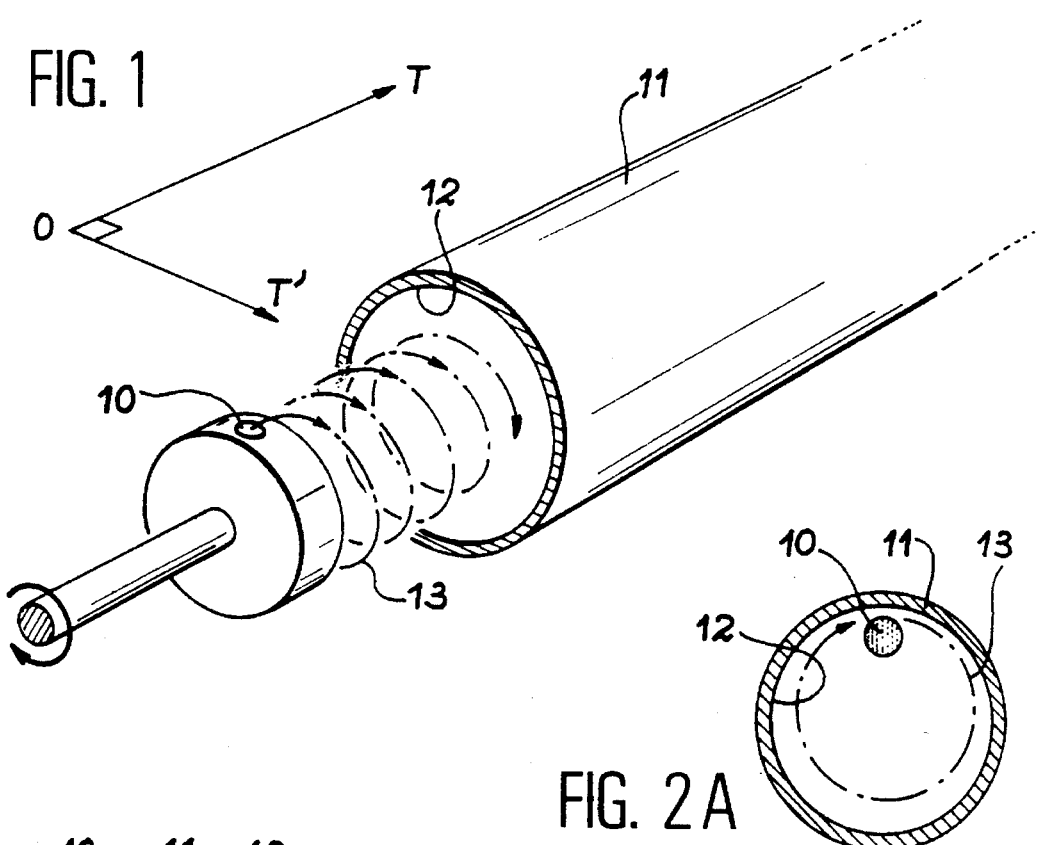
FIG. 1 Illustrates the displacement of the eddy current transducer used in the process according to the invention.

As shown in FIG. 1, the eddy current transducer used comprises an absolute point probe 10. This probe has a coil, whose axis is perpendicular to the inner surface 12 of a tube 11. It carries out a scan 13 of the complete surface following a helical movement. In such a probe 10, any variation in the interior of the wall of the conductive material tube 11 (size change, conductivity variation) modifies the intensity or passage of the eddy currents and consequently the coil impedance.

Thus, as a result of this scan 13, the inner surface 12 of the tube 11 is broken down into a certain number of elementary measurement zones separated by a certain acquisition gap. In the case of a surface referenced by two coordinates OT and OT', as illustrated in FIG. 1, these zones e.g. form a squaring of the surface, whose fineness is dependent on the size of the sampling. This squaring leads to the association with the examined surface of a table of sampled values, recorded during the movement of the probe 10 in front of the surface 12. Thus, if the probe 10 travels along a path 13, the table is filled row by row along the path. In other words, with each box of the table are associated the coordinates T and T' of the probe 10 and the sample value of the signal which it supplies in the position, the filling direction of the boxes being imposed by the path followed by the probe. The scan of the surface by the probe is therefore accompanied by an acquisition of data constituting sampled values of the signal supplied by the probe and recorded during the displacement of the latter.

It is possible to obtain a representation of the data by a map or three-dimensional image of the signal. However, such a map obtained as a result of the scan of the tube by means of the probe is highly disturbed by a background signal comprising low frequency components due to geometrical variations and at present no fault analysis tool exists.

Figure 2A:
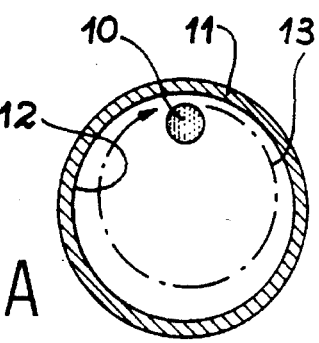
FIGS. 2A–2C Illustrates several causes of background noise existing on the output signal of the eddy current transducer.
Figure 2B:
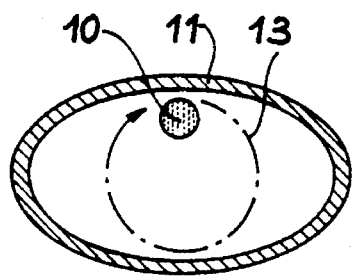
Figure 2C:
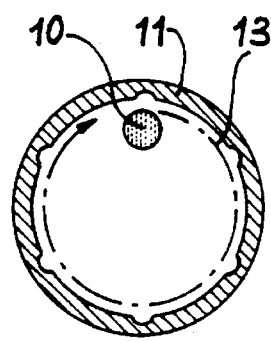

Such a background noise can have several causes and in particular:

an offcentred displacement 13 of the probe 10 with respect to the periphery of the tube 11, as represented in FIG. 2A, an out of true tube 11, as shown in FIG. 2B and this can be observed during the machining of tubes or as a result of operational stresses, a pilger-rolled tube 11 (stretching of the tube with a six-toothed tool), as shown in FIG. 2C.

The process according to the invention aims to improve the signal to noise ratio of the image by subtracting from the image the low frequency components characteristic of the background noise. To carry this out, the image will be considered as a sum of elementary surfaces and from it are subtracted all the characteristic components of the background noise.

The development of this process involves the choice of a function base. For this purpose it is necessary to take into account the physical origin of the background noise disturbing the image. The gap variations (transducer—surface distance) are periodic in accordance with the circumference of the tube and generate sinusoidal oscillations. The elementary surface base is thus constructed from unidimensional sinusoidal functions, both for the circumferential and the longitudinal direction. However, along the latter direction the periodicity is imposed, which can give rise to edge effects. To avoid these, a "truing" preprocessing is carried out, which makes it possible to render equivalent the first and final columns of the image.

The surface which it is wished to resolve does not constitute a continuous zone, because there is an isolation of a fault window contained in the image. The information inherent in the fault window or slot must not appear in the calculation of the projection coefficients, which must only reflect the background noise components. Therefore the working surface is the image deprived of the fault window.

Several function bases are then necessary:

a function base $g_{i,j}$ defined by portions on the same zone as the image deprived of the fault window. It is on the basis of these functions that a calculation takes place of the projection coefficients for each component, a function base $h_{i,j}$ defined over the entire zone (continuous) of the image, these functions making it possible to reconstruct the background noise on the complete image.

Consideration is to be given to the following notations:

$X(t,t')$: starting image, in which $t$ and $t'$ represent the coordinates of the points and $X(t,t')$ the amplitude in these coordinates.

$g_{i,j}(t,t')$: bidimensional functions representing elementary sinusoidal surfaces defined on the image deprived of the window.

$h_{i,j}(t,t')$: bidimensional functions representing the elementary sinusoidal surfaces defined on the entire image.

$a_{i,j}$: projection coefficients between the image $X(t,t')$ and the base surface $g_{i,j}$.

All these processing operations of the process according to the invention implies a first fault window detection phase and then, on the basis of the remaining map points, the reconstruction of the background noise surface on the complete image. The base surfaces used are defined by the unidimensional sinusoidal function products. For this purpose there is a resolution of the image related to a Fourier series resolution, in order to determine the most representative components from an energy standpoint and the reconstructed final noise surface is the sum of the base surfaces weighted by the corresponding Fourier coefficients. The processing of the signal according to the invention considers the image as a weighted sum of the elementary surfaces. It determines the weighting coefficients for the different elementary surfaces and obtains a noise surface, which is subtracted from the complete starting image. A truing preprocessing is carried out beforehand on the noisy signal.

Figure 3:
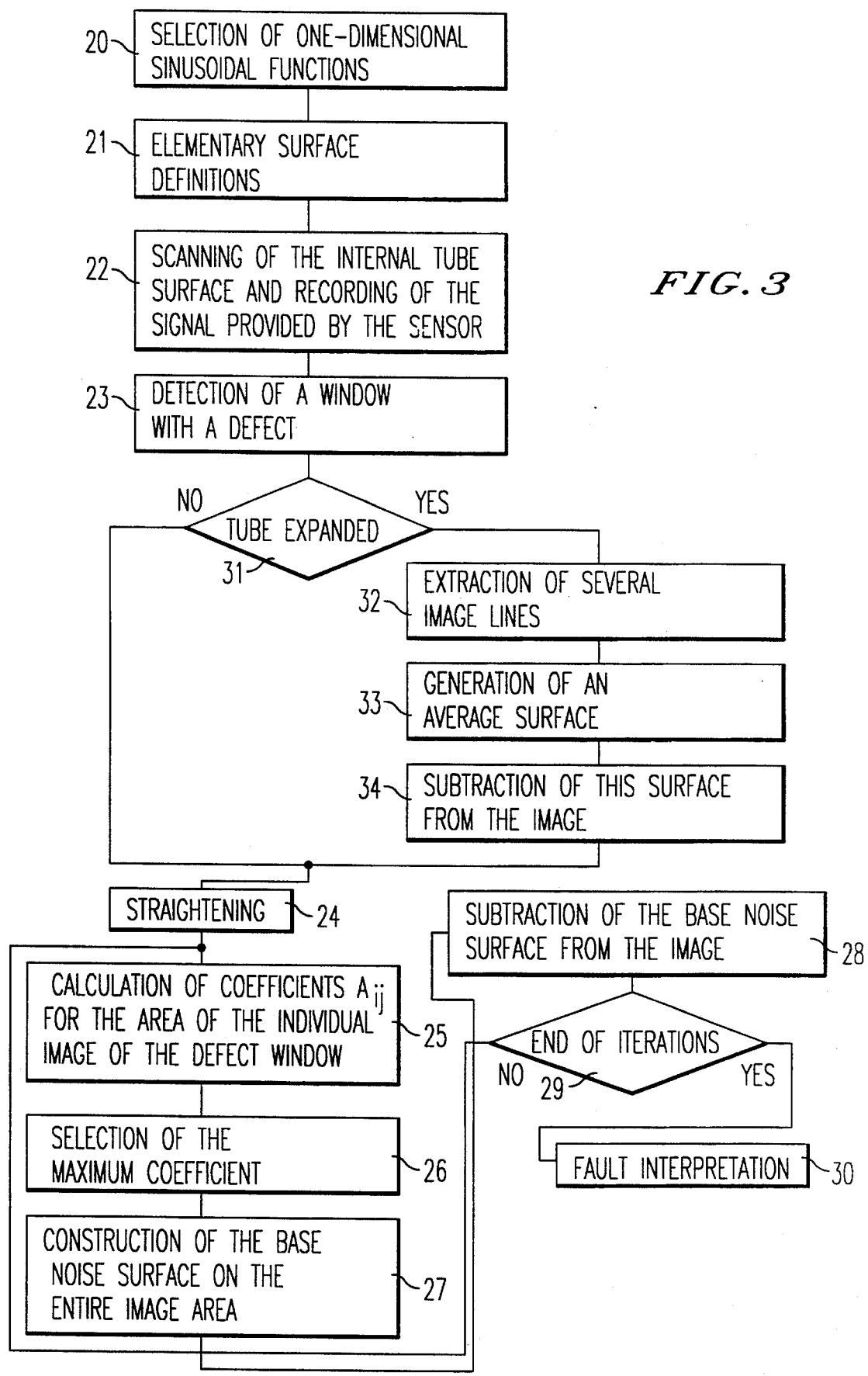
FIG. 3 Illustrates a flow chart concerning the operation of the process according to the invention.

Thus, after calibration and alignment of the probe 10, the algorithm of the process according to the invention shown in FIG. 3 comprises:

a stage 20 of choosing these basic unidimensional sinusoidal functions, a stage 21 of the defining elementary surfaces, a stage 22 of scanning the inner surface 12 of the tube and recording the signal supplied by the probe 10, a stage 23 of detecting a window or slot containing a fault or defect, a truing stage 24, the truing being a prior processing rendering equivalent the first and last columns of the image and for each row of the map calculation takes place of the line passing through the two points of its ends and the line is then subtracted from the corresponding row, a stage 25 of calculating coefficients $a_{i,j}$ for each i and j, the coefficients being the projection of the entire surface $X(t,t')$ deprived of the fault window on the elementary surfaces $$a_{i,j}=<X,g_{i,j}>=\int X(t,t') \cdot g_{i,j}(t,t') \cdot dt \cdot dt'$$

this being a Fourier series resolution, to within a coefficient and it is possible to refer to a resolution related to a Fourier series resolution, a stage 26 of choosing the maximum coefficient $a_{k,l}=\max(a_{i,j})$, a stage 27 of constructing the background noise surface on the complete image from the information available outside the fault window, a stage 28 of subtracting the total noise surface, including in the fault zone, in order to subtract it from the original image, subtraction taking place of the component corresponding to the coefficient $a_{k,l}$:

$$Res(t,t')=X(t,t')-a_{k,l}*h_{k,l}(t,t')$$

This residual image $Res(t,t')$ becomes the image $X(t,t')$ to be resolved. Iteration takes place on the four final stages to obtain all the background noise components, using a test 29.

Finally, the process according to the invention comprises a fault interpretation stage 30. The corrected image is then skeletized by a conventional process, which supplies the fault direction and size. On the basis of this corrected image, it is possible to access the phase of the signal and therefore the depth of the fault (conventional representation in the impedance plane).

Figure 4:
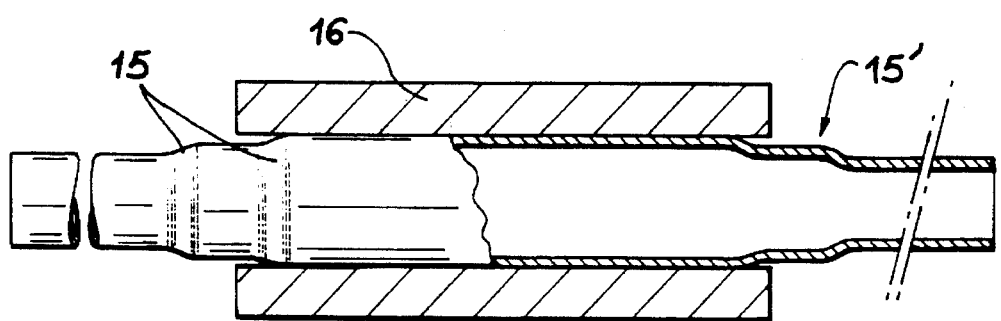
FIG. 4 Illustrates an expanded tube.

Another problem arises when the maps correspond to expansion transition zones 15, 15' of a tube, e.g. introduced in a braced plate 16, as shown in FIG. 4. They then have at least one "step" (in this case two steps corresponding to the two expansion zones 15 or 15'), whereof the front is very inflexible. In this case, the sinusoidal functions only approach the image in a very mediocre manner and do not make it possible to eliminate the effect of the tube expansion.

In order to bring about the suppression of the expansion step or steps, a calculation takes place of the average profile in accordance with the longitudinal axis, based on about ten longitudinal rows of the image. The process according to the invention then has, following a test 31, several successive stages:

a stage 32 of extracting several longitudinal rows from the image, a stage 33 of generating an average surface, a stage 34 of subtracting the surface from the original image.

Figure 5:
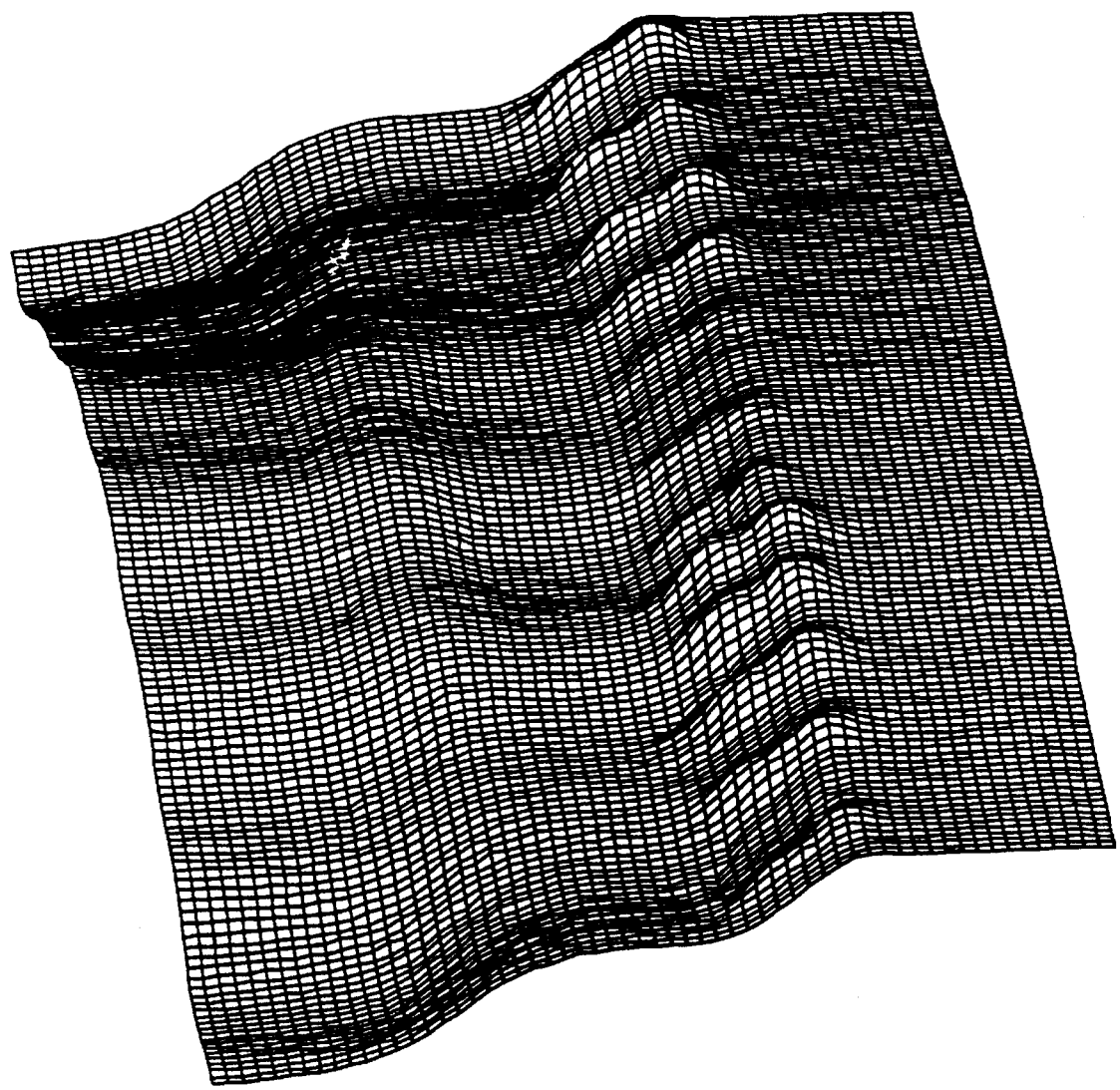
FIGS. 5 & 6 Respectively illustrate a map before processing and after processing according to the process of the invention.
Figure 6:
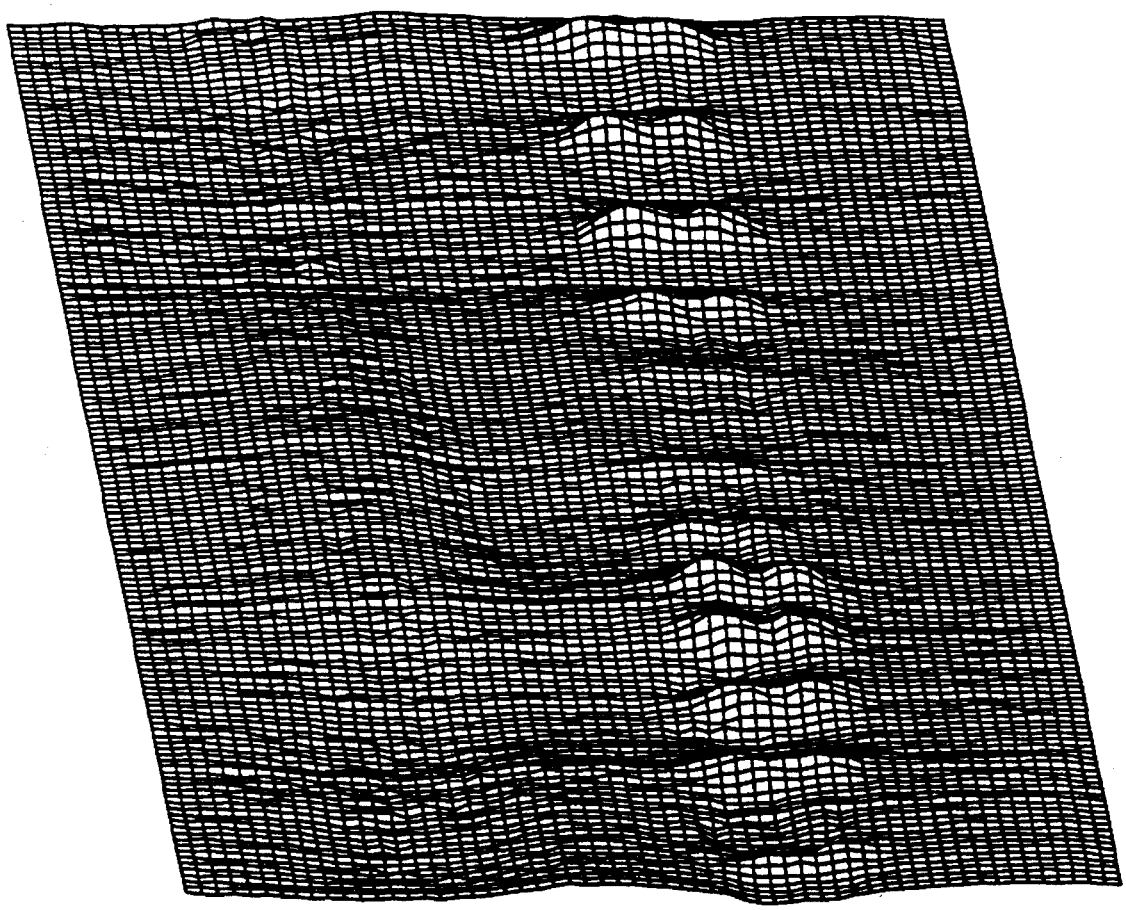

Thus, the process according to the invention makes it possible to pass from an image like that of FIG. 5 to an image like that of FIG. 6.

Thus, at the end of the process according to the invention there is an interpretation of the fault 30. Information is obtained on the "architecture" of the fault, namely its direction, size and depth. The use of mathematical morphology tools on the maps gives information relative to the first two parameters, i.e. orientation and size. The information concerning the depth cannot be obtained from the electromagnetic surfaces. It is necessary to return to the complex plan and study the LISSAJOU curves obtained from the rows and columns extracted from the maps (rows X and Y). The process of the invention consists of applying a skeletization algorithm to the image. Such algorithms are more particularly described in the work entitled "Morphological Methods in Image and Signal Processing" by Ch. R. Giardina and E. R. Dougherty (Prentice Hall).

Thus, FIG. 7A is a network of six longitudinal faults, five being faults 40 of length 6 mm and depth 30% and the sixth being a fault 41 of length 12 mm and depth 60%, coupled with a circumferential fault 42 of depth 60% located on the inner surface of the tube.

FIG. 7B gives the original map.

FIG. 7C gives the skeleton of the image.

Thus, the process according to the invention makes it possible to reject a tube before use or close it again following installation in a steam generator, if the fault measured has characteristics (length, orientation, depth) exceeding certain thresholds. This is the case when the fault, oriented in the circumferential direction, extends over the entire circumference and when the fault is oriented in the longitudinal direction and its length exceeds 8 or 9 mm.

We claim:

1. A system for determining a defect in a conductive material tube comprising:

means for defining an elementary surface, wherein the elementary surface is a product of two basic unidimensional functions respectively defined in accordance with a longitudinal direction and a circumferential direction of the inner surface of the conductive material tube;

an eddy current absolute point transducer for scanning an inner surface of the conductive material tube in an order of measuring zones to generate measurement signals;

means for recording sample values of the measurement signals for each of the measuring zones, to generate a three-dimensional image representation of the scanned inner surface of the conductive material tube;

means for constructing a background noise signal of the three-dimensional image representation;

means for subtracting the background noise signal from the three-dimensional image representation to generate a final image; and means for determining a fault in the inner surface of the conductive material tube based on the final image.

2. The system according to claim 1, wherein the two basic unidimensional functions are sinusoidal functions.

3. A system for determining a defect in a conductive material tube comprising:

means for defining an elementary surface;

an eddy current absolute point transducer for scanning an inner surface of the conductive material tube in an order of measuring zones to generate measurement signals;

means for recording sample values of the measurement signals for each of the measuring zones, to generate a three-dimensional image representation of the scanned inner surface of the conductive material tube;

means for constructing a background noise signal of the three-dimensional image representation;

means for subtracting the background noise signal from the three-dimensional image representation to generate a final image;

means for determining a fault in the inner surface of the conductive material tube based on the final image; and means for detecting a window containing a fault after defining the elementary surface, the means for defining the elementary surface operating on a first surface base $g_{i,j}$ defined by portions on a zone of an image deprived of a fault window, and a second surface base $h_{i,j}$ defined on an entire zone of the image, where i and j are integers.

4. The system according to claim 3, wherein following the detection of the fault window, further comprising means for truing preprocessing to render first and final columns of the three-dimensional image equivalent.

5. The system according to claim 4, wherein the truing preprocessing subtracts a line joining extreme points of the three-dimensional image equivalent.

6. The system according to claim 3, further comprising means for a truing preprocessing and a tube expansion signal suppression preprocessing prior to resolving the three-dimensional image representation.

7. The system according to claim 6, wherein said tube expansion signal suppression preprocessing extraction takes place on several longitudinal rows of the three-dimensional image representation outside of the fault window.

* * * * *